US009188560B2

(12) United States Patent
Liu et al.

(10) Patent No.: US 9,188,560 B2
(45) Date of Patent: *Nov. 17, 2015

(54) ELECTRO-DIFFUSION ENHANCED BIO-MOLECULE CHARGE DETECTION USING ELECTROSTATIC INTERACTION

(71) Applicant: The Board of Trustees of the Leland Stanford Junior University, Palo Alto, CA (US)

(72) Inventors: Yang Liu, San Jose, CA (US); Robert W. Dutton, Palo Alto, CA (US); Roger T. Howe, Los Gatos, CA (US)

(73) Assignee: THE BOARD OF TRUSTEES OF THE LELAND STANFORD JUNIOR UNIVERSITY, Stanford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/516,290

(22) Filed: Oct. 16, 2014

(65) Prior Publication Data

US 2015/0102830 A1    Apr. 16, 2015

Related U.S. Application Data

(62) Division of application No. 12/822,971, filed on Jun. 24, 2010, now Pat. No. 8,864,969.

(60) Provisional application No. 61/220,496, filed on Jun. 25, 2009.

(51) Int. Cl.
*G01N 27/04*    (2006.01)
*G01N 33/68*    (2006.01)
(Continued)

(52) U.S. Cl.
CPC    *G01N 27/04* (2013.01); *C12Q 1/68* (2013.01); *G01N 33/48721* (2013.01); *G01N 33/68* (2013.01)

(58) Field of Classification Search
CPC ............................. G01N 27/62; G01N 33/48
See application file for complete search history.

(56) References Cited

U.S. PATENT DOCUMENTS 5,082,564 A    1/1992    Halff et al.
6,413,792 B1    7/2002    Sauer et al.
(Continued)

FOREIGN PATENT DOCUMENTS

WO    2007041692 A2    4/2007

OTHER PUBLICATIONS

P. Bergveld, "A critical evaluation of direct electrical protein detection methods," Biosensors and Bioelectronics; 6(1), pp. 55-72 (1991).

(Continued)

*Primary Examiner* — Jennifer Dieterle (57) ABSTRACT

According to one aspect, the disclosure is directed to an example embodiment in which a circuit-based arrangement includes a circuit-based substrate securing a channel, with an effective width that is not limited by the Debye screening length, along a surface of the substrate. A pair of reservoirs are included in or on the substrate and configured for containing and presenting a sample having bio-molecules for delivery in the channel. A pair of electrodes electrically couple a charge in the sample to enhance ionic current flow therein (e.g., to overcome the electrolyte screening), and a sense electrode is located along the channel for sensing a characteristic of the biological sample by using the electrostatic interaction between the enhanced ionic current flow of the sample and the sense electrode. Actual detection occurs by using a charge-signal processing circuit to process the sensed charge signal and, therefrom, provide an output indicative of a signature for the bio-molecules delivered in the channel.

24 Claims, 6 Drawing Sheets

(51) Int. Cl.
*C12Q 1/68* (2006.01)
*G01N 33/487* (2006.01)

(56) References Cited

U.S. PATENT DOCUMENTS

| | | | |
|---|---|---|---|
| 7,001,792 B2 | 2/2006 | Sauer et al. |
| 2003/0211502 A1 | 11/2003 | Sauer et al. |
| 2004/0149568 A1 | 8/2004 | Huang et al. |
| 2005/0202444 A1 | 9/2005 | Zhu |
| 2005/0252857 A1 | 11/2005 | Wilson et al. |
| 2006/0049105 A1 | 3/2006 | Max |
| 2006/0154399 A1 | 7/2006 | Sauer et al. |
| 2007/0159156 A1 | 7/2007 | Hu et al. |
| 2007/0238112 A1 | 10/2007 | Sohn et al. |
| 2008/0119366 A1 | 5/2008 | Sauer et al. |
| 2008/0187915 A1 | 8/2008 | Polonsky et al. |
| 2009/0314718 A1 | 12/2009 | Sparrow et al. |
| 2010/0096268 A1 | 4/2010 | Ling et al. |
| 2011/0147314 A1 | 6/2011 | Kippeny et al. |
| 2012/0031763 A1 | 2/2012 | Ohmi et al. |
| 2013/0034489 A1 | 2/2013 | Gilliam et al. |

OTHER PUBLICATIONS

J.J. Kasianowicz, E. Brandin, D. Branton, and D.W. Deamer, "Characterization of individual polynucleotide molecules using a membrane channel," Proc. Natl. Acad. Sci., vol. 93, No. 24, pp. 13770-13773 (Nov. 1996).
J. Goo, C. Choi, F. Danneville, E. Morifuji, H.S. Momose, Y. Zhiping, H. Iwai, T.H. Lee, and R.W. Dutton, "An accurate and efficient high frequency noise simulation technique for deep submicron MOSFETs", IEEE Trans. On Electron Devices, vol. 47, No. 12, pp. 2410-2419 (Dec. 2000).
A. Meller, L. Nivon, and D. Branton, "Voltage-driven DNA translocations through a nanopore," Physical Review Letters, vol. 86, No. 15, pp. 3435-3438 (2001).
G. De Geronimo, P. O'Connor, V. Radeka, B. Yu, "Front-end electronics for imaging detectors", Nuclear Instruments and Methods in Physics Research, A 471 pp. 192-199 (2001).
M. Shim, N. Wong Shi Kam, R. Chen, Y. Li, and H. Dai, "Functionalization of Carbon Nanotubes for Biocompatibility and Biomolecular Recognition," American Chemical Society, Nano Letters, vol. 2, No. 4, pp. 285-288 (2002).
M. J. Schoning and A. Poghossian, "Recent advances in biologically sensitive field-effect transistors (BioFETs)," Analyst, vol. 127, pp. 1137-1151 (2002).
A.J. Storm, J. Chen, X. Ling, and D.C. Zandbergen, "Fabrication of solid-state nanopores with single-nanometer precision," Nature Mater.; vol. 2, pp. 537-540 (Aug. 2003).
J. Hahm and C. M. Lieber, "Direct ultrasensitive electrical detection of DNA and DNA sequence variations using nanowire nanosensors," Nano Letters, vol. 4, No. 1, pp. 51-54 (2004).
Z. Li, Y. Chen, X Li, T I Kamins, K. Nauka and R.S. Williams, "Sequence specific label-free DNA sensors based on silicon nanowires," Nano Letters, vol. 4, No. 2, pp. 245-247 (2004).
M. C. Cheng et al., "Nanotechnologies for biomolecular detection and medical diagnostics," Current Opinion in Chemical Biology, vol. 10, pp. 11-19 (2006).
A.Talasaz, M. Nemat-Gorgani, Y. Liu, P. Stahl, R.W. Dutton, M. Ronaghi, and R.W. Davis, "Prediction of protein orientation upon immobilization on biological and nonbiological surfaces," Proc Natl Acad Sci, vol. 103, No. 40, pp. 14773-14778 (2006).
E. Stern et al., "Label-free immunodetection with CMOS-compatible semiconducting nanowires," Nature, vol. 445, pp. 519-522 (2007).
Y. Liu, J. Sauer, and R. Dutton, "Effect of Electrodiffusion Current Flow on Electrostatic Screening in Aqueous Pores," J. Appl. Phys. 103, pp. 084701-1-03 (2008).
Y. Liu, K. Lilja, C. Heitzinger, and R. Dutton, "Overcoming the Screening-Induced Performance Limits of Nanowire Biosensors: A Simulation Study on the Effect of Electro-Diffusion Flow," Electron Devices Meeting, IEDM 2008, IEEE International, pp. 1-4 (2008).
P. R. Nair and M. A. Alam, "Screening-limited response of nanobiosensors," Nano Letters, vol. 8, No. 5, pp. 1281-1285 (2008).
S. Jae Kim, S. Hee Ko, K. Hyoung Kang, and J. Han, "Direct seawater desalination by ion concentration polarization," Nature Nanotechnology, vol. 5, pp. 297-301 (Apr. 2010).
Y. Liu, D. D Huber, and R Dutton, "Limiting and overlimiting conductance in field-effect gated nanopores," Appl. Phys. Lett. 96, 253108 (2010).
F. Danneville, H. Happy, G. Dambrine, J.-M. Belquin, A. Cappy, "Microscopic noise modeling and macroscopic noise models: how good a conection?", IEEE Trans. on Electron Devices, vol. 41, No. 5, pp. 779-786 (May 1994) (Abstract Only).
W. Huang, S. Taylor, K. Fu, Y. Lin, D. Zhang, T. Hanks, A. Rao, and Y. Sun, "Attaching Proteins to Carbon Nanotubes via Diimide-Activated Amidation," American Chemical Society, Nano Letters, Mar. 16, 2002, 2 (4), pp. 311-314.
E. Souteyrand, J.P. Cloarec, J.R. Martin, C. Wilson, I. Lawrence, S. Mikkelsen, and M.F. Laurence, "Direct detection of the hybridization of synthetic homo-oligomer DNA sequences by field effect," J. Phys. Chem. B, vol. 101, pp. 2980-2985 (1997).
J. Li, D. Stein, C. McMullan, D. Branton, M. Aziz, and J. Golovshenko, "Ion-beam sculpting at nanometer length scales," Nature, vol. 412(6843), pp. 166-169 (2001).
P. Bergveld, "Thirty years of ISFETOLOGY: what happened in the past 30 years and what may happen in the next 30 years," Sensors and Actuators B, vol. 88, pp. 1-20 (2003).
Stefan Howorka, Stephen Cheley & Hagan Bayley, "Sequence-specific detection of individual DNA strands using engineered nanopores", Nature Biotechnology 19, 636-639 (Jul. 1, 2001) Abstract Only.
S Ingebrandt, Characterization of the cell-transistor coupling, dissertation thesis, Johannes Gutenberg University Mainz, Germany (2001). (divided into 3 uploads due to length of dissertation).
Mou-shan Chen, "Wien effect in mixed strong electrolytes", J. Chem. Phys. 68(12), Jun. 15, 1978.

ELECTRO-DIFFUSION ENHANCED BIO-MOLECULE CHARGE DETECTION USING ELECTROSTATIC INTERACTION

RELATED PATENT DOCUMENTS

This patent document is a divisional, under 35 U.S.C. §120, of U.S. patent application Ser. No. 12/822,971 filed on Jun. 24, 2010 (U.S. Pat. No. 8,864,969), which claims the benefit, under 35 U.S.C. §119(e), of U.S. Provisional Patent Application Ser. No. 61/220,496 filed on Jun. 25, 2009, and entitled "Electro-Diffusion Enhanced Bio-Molecule Charge Detection Using Long-Range Electrostatic Interaction;" this patent document and the Appendices A-D filed in the underlying provisional application are fully incorporated herein by reference.

FIELD

The present disclosure is generally directed to methods and apparatuses, including but not limited to semiconductors, providing for and using electrical detection of bio-molecules charges.

BACKGROUND

The electrical detection of bio-molecules is currently an active research field. Two types of detection approaches are typically used. The first type is based on translocation of bio-molecules through nanometer-size ion channels across biological membranes or solid-state pores across dielectric membranes. The detection mechanism is based on the blockage of the electrical conductance of the pores during translocation events. This approach is capable of single bio-molecule analysis. However, due to the small sizes of the bio-molecules (DNAs in the referred studies), the size of the pores is required to be small (<~10 nm) for appreciable current blockage signals, which imposes enormous fabrication challenges. The second type uses field effect to detect the biological charge of bio-molecules that are specifically immobilized to the sensor surface; this includes both planar ISFET structure and, more recently, nanowire structures. This affinity-type approach often detects the ensemble average signal of the immobilized bio-molecules. Electrolyte screening is known to impose a fundamental limit on its charge sensing capabilities at physiological condition. As an example, the characteristic Debye screening length in a physiological condition (~100 mM salt concentration) is ~1 nm.

In other research efforts, scientists have described DNA sequencing devices that use semiconductor field effect transistors at the surface of an opening or recess for charge detection of analytes flowing by in the close vicinity under electrophoresis process. Just as the ISFET type sensing scheme, such proposed devices are still limited by the electrolyte screening since no mechanisms are identified or designed to overcome that limit. Their charge sensing operation is dependent on the close proximity (~Debye length) of bio-molecules to the sensing elements. Such devices propose relatively small-size openings (e.g., <~10 nm), which enormously complicates the device fabrication steps. These devices also use metal and insulator layers to replace the p-doped or n-doped semiconductor regions. The operation of this type of device is based on the principle that the field effect will change the tunneling current across the insulator layer from one metal layer to another.

Accordingly, there is need for apparatuses and methods, involving the detection of bio-molecule charges, that overcome these and other limitations.

SUMMARY

Certain aspects of the present disclosure are directed to apparatuses and methods that overcome the above-mentioned and other issues. Consistent therewith, specific apparatuses and methods involve the detection of bio-molecule charges based on their long-range electrostatic interaction. In one of various embodiments, such detection is directed to bio-molecule charges with significantly-enhanced sensitivity by exploiting electro-diffusion ionic current flow in micro-machined channels and other types of channels (e.g., laterally- and vertically-oriented).

According to a specific example, the present disclosure is directed to implementations of an apparatus and/or method involving the enhanced detection of charges of bio-molecules traversing a channel situated adjacent a sense electrode and between biasing electrodes; such charge detection is not limited by the electrolyte screening. In more specific embodiments of the disclosure, aspects include (operating alone or in combinations thereof): the channel being largely compatible with conventional manufacturing requirements (e.g., in terms of foundry and micro-electromechanical system processes and/or feature size); the bio-molecule charges being sensed using a long-range electrostatic interaction; the electrodes being controlled to manipulate the charges, the charge screening and/or movement of the bio-molecules for facilitating detection; the inclusion of AC modulation and lock-in techniques for enhanced sensing applications; and the detection of bio-molecule charges at the single-molecule level.

In connection with other specific embodiments, the disclosure is directed to a system for detecting bio-molecule charges based on their electrostatic interaction. The system includes an integrated-circuit arrangement that detects bio-molecule charges, the arrangement includes a circuit-supporting substrate, at least one reservoir configured for containing and presenting a sample having bio-molecules, first and second electrodes configured for electrically coupling a charge in the sample, at least one sense electrode located along the channel, and a charge-signal processing circuit. The circuit-supporting substrate includes a channel that is not limited by the Debye screening length. In one implementation, the channel is located along a surface of the substrate (e.g., micro-machined along the surface or formed via an attached separate member) and, in another implementation, the channel is formed using a through hole in the substrate. The reservoir is also configured for delivering the bio-molecules in the channel, and the biasing electrodes are configured for enhanced ionic current flow, e.g., overcoming the electrolyte screening, and therefore enhancing the electrically coupling a charge in the sample to the sense electrodes. In response to the sense electrode detecting a characteristic of the biological sample based on the electrostatic interaction with the sample, the charge-signal processing circuit communicatively provides an output indicative of a signature for the bio-molecules delivered in the channel. In a more specific implementation, the integrated-circuit arrangement has at least one of the electrodes buried in the substrate adjacent the channel and used in this configuration for charge sensing and/or bio-molecule movement control. In another more specific implementation, the integrated-circuit arrangement employs nanostructures (e.g., nanowires or nanotube arrays)

along the surface channel, e.g., along the bottom of a laterally-arranged channel, for sensing charges of the translocating biomolecules.

Other embodiments are indicated by way of the examples described herein, and by way of the contemplated claims and papers appended hereto.

The above summary is limited to characterizing certain aspects and is not intended to describe each illustrated embodiment or every implementation of the present disclosure. The figures and detailed description that follow, including that described in the appended claims, more particularly exemplify embodiments in support of the disclosure.

BRIEF DESCRIPTION OF THE DRAWINGS

The present disclosure may be more completely understood in consideration of the detailed description of various embodiments of the disclosure that follows in connection with the accompanying drawings as follows.

Also consistent with embodiments of the present disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

The present disclosure is believed to be useful for a variety of applications involving the sensing/detection of bio-molecules from their characteristic charges. As nonlimiting examples, these applications include gene sequence applications such as those involving the detection of DNA hybridization based on oligomer charges doubling after hybridization, applications involving immune responses based on change of charges from antibody-antigen binding, detection of protein phosphorylation as in applications involving neutral hydroxyl group replaced by negatively charged phosphate and other applications for general charge-based particle detection such as charged particles in industrial waste. While the present disclosure is not limited to such applications, various aspects of the disclosure may be appreciated through a discussion of various examples using this context.

Aspects of the present disclosure are directed to the sensing and detection of bio-molecules in a sample by bio-molecule charges with significantly enhanced sensitivity. By exploiting electro-diffusion ionic current flow channels without being limited by the Debye screening length, embodiments involve use of electrodes for electrically coupling a charge to and for sensing, based on long-range electrostatic interaction, a characteristic of the sample. Biological macromolecules such as DNAs and proteins carry a certain amount of charges in a physiological electrolyte solution, and the electrical sensing of such biological charges is used to gain access to direct detection and analysis of biological species, ultimately at a single-molecule level.

Certain embodiments of the present disclosure concern the Debye-Huckel theory which dictates that charge sensing is only possible within a few Debye lengths from the biomolecules (one Debye length is ~1 nm at 100 mM electrolyte concentration that approximates the physiological condition); this theory suggests a detection-sensitivity limit of electrostatic screening by electrolyte counter-ions. Consistent with certain implementations, such a limit can be overcome by carrying out charge detection under an electrical current flow environment in channels having an effective width that is not limited by the Debye screening length; these channels include, e.g., lateral channels such as micro-machined surface channels and vertical channels as in substrate vias. Recently-published surprising simulation results made in connection with the present disclosure establish that the presence of steady-state electro-diffusion ionic flow can dramatically suppress the electrolyte screening and therefore improve the signal levels. Certain aspects consistent with this approach are based on long-range electrical sensing to significantly relax fabrication complexity and to provide compatibility with integrated circuit (IC) processes. In this regard, these aspects of the present disclosure are highly suitable for low-cost, point-of-care medical diagnostic applications. For further information regarding charge detection of bio-molecular substances and these surprising simulation results, reference may be made to, Y. Liu, K. Lilja, C. Heitzinger, and R. Dutton, *Overcoming the Screening-Induced Performance Limits of Nanowire Biosensors: A Simulation Study on the Effect of Electro-Diffusion Flow*, Electron Devices Meeting, IEDM 2008, IEEE International, pp. 1-4 (2008); this document forms part of this patent document and is attached to the above-noted provisional patent document as Appendix A.

Figures 1A, 1B, 1C:
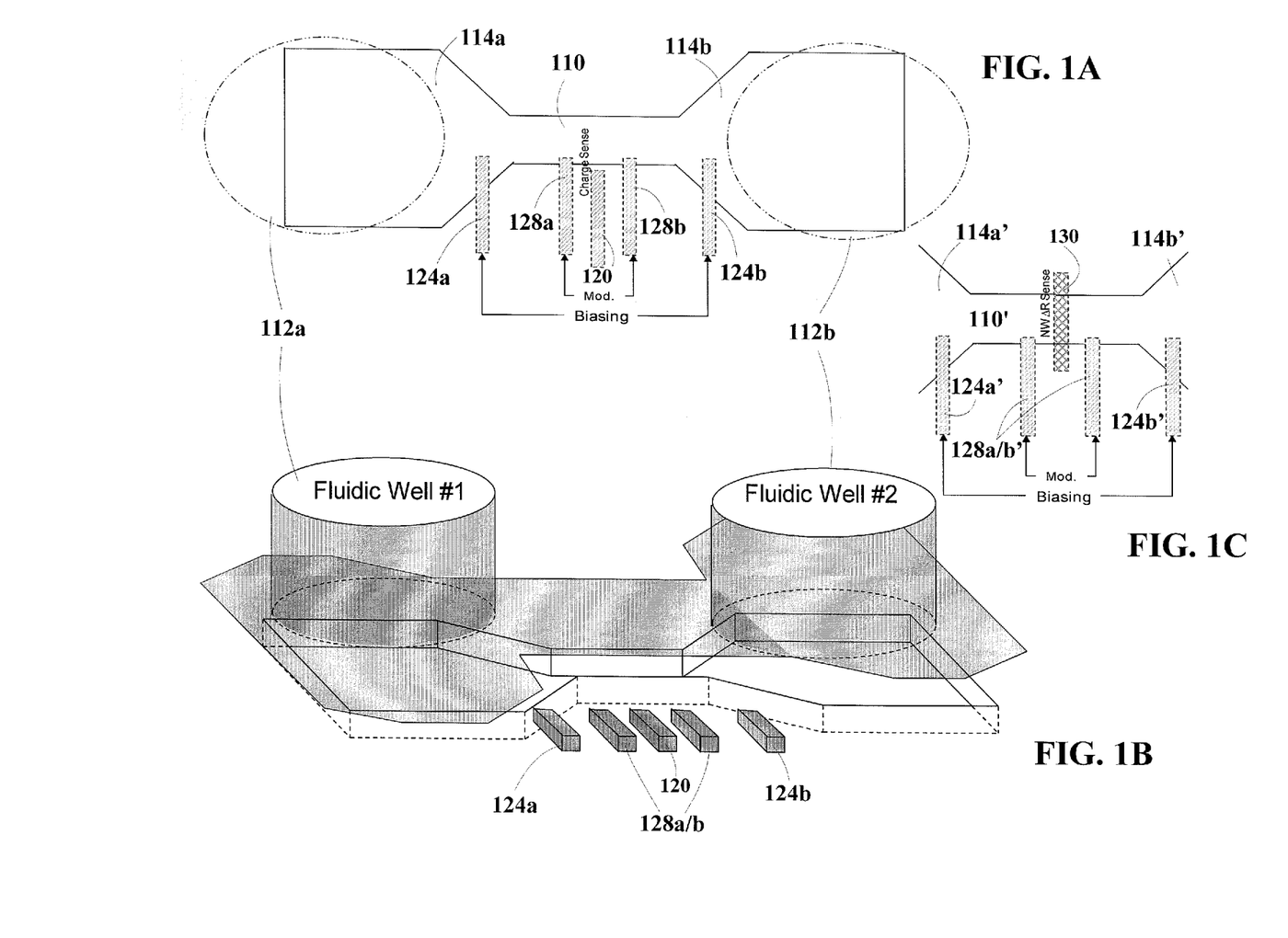
FIGS. 1a, 1b and 1c are illustrations of exemplary biosensor apparatuses consistent with the present disclosure, with FIGS. 1a and 1b respectively providing a plan view and a perspective view of an exemplary biosensor apparatus and FIG. 1c showing a plan view of an alternative implementation for sensing electrodes in another exemplary biosensor apparatus.

Turning now to the drawings, FIGS. 1a and 1b are respective plan and perspective views of an exemplary biosensor apparatus according to the present disclosure. Channel 110 is depicted between (delivery) reservoir 112a and (receiving) reservoir 112b, with fluidic interfaces 114a and 114b connecting sample fluid between the channel 110 and the associated reservoir 112a/112b. A charge-sense electrode 120 is buried near the bottom of the channel 110 and configured to sense charges on the analytes (charged biomolecules) in response to voltage(s) applied to biasing electrodes 124a-b by a voltage bias circuit (not illustrated). The sense electrode 120 is connected to a read-out circuit (not illustrated) that includes charge sensitive amplifiers and, following, stages of signal-multiplexing and signal-processing units. By implementing the channel 110 with a width that is not limited by the Debye screening length, an electrolyte solution is introduced to fill the channel via (delivery) reservoir 112a and fluidic interface 114a, a voltage bias circuit controls the biasing electrodes 124a-b (placed in the solutions in each of the reservoirs), and the analytes are introduced in one of the chambers and are subjected to an electric field ensuing from the voltage being applied between (or across) the two biasing electrodes. The biomolecules travel across the channel to the other side of the channel by electrophoresis. When the biomolecules travel by the sense electrodes, image charges are induced in the electrode by field effect, which leads to signals in the read-out circuits. The multiplexing of signals from the multiple sense electrodes are used to enhance the signal levels and extract information on the travelling speed of the analytes. As discussed in connection with the included appendices, the experimental studies and embodiments demonstrate remarkable and unexpected selectivity and sensitivity.

An important option for the above-illustrated detector arrangements involves use of modulation circuit for driving modulation electrodes 128a and 128b. This modulation is used in combination with a signal lock-in circuit to detect and lock onto the correct (modulated) signal as the biomolecules travel across the channel to the other side of the channel by electrophoresis. When the biomolecules travel by the sense electrodes, image charges are induced in the electrode by field effect, which leads to discernment of the modulated signals in the read-out circuits. This discernment is provided for any of various signal lock-in circuits including, for example, largely conventionally-implement phase-locked or frequency-locked loop circuits.

FIG. 1c illustrates an alternative embodiment in which a charge-sense electrode 130 (as opposed to the charge-sense electrode 120 of FIG. 1b) is a nanostructure (such as a nanowire, carbon nanotube or other reactive nanostructure) which may be functionalized to provide a detectable conductance-type reaction as the biomolecules travel through the channel by electrophoresis. In this regard, the sense electrode 130 acts like a resistor that changes resistance in the presence of a certain type of complementary molecule.

For an example of work performed in this area of nanostructure functionalization, reference may be made to the articles: W. Huang, S. Taylor, K. Fu, Y. Lin, D. Zhang, T. W. Hanks, Apparao M. Rao, and Ya-Ping Sun, "*Attaching Proteins to Carbon Nanotubes via Diimide-Activated Amidation*," American Chemical Society, Nano Letters, 2 (4), pp. 311-314 (Mar. 16, 2002), and M. Shim, N. Wong Shi Kam, R. J. Chen, Y. Li, and H. Dai, "*Functionalization of Carbon Nanotubes for Biocompatibility and Biomolecular Recognition*," American Chemical Society, Nano Letters (Jan. 21, 2002).

Figure 2A:
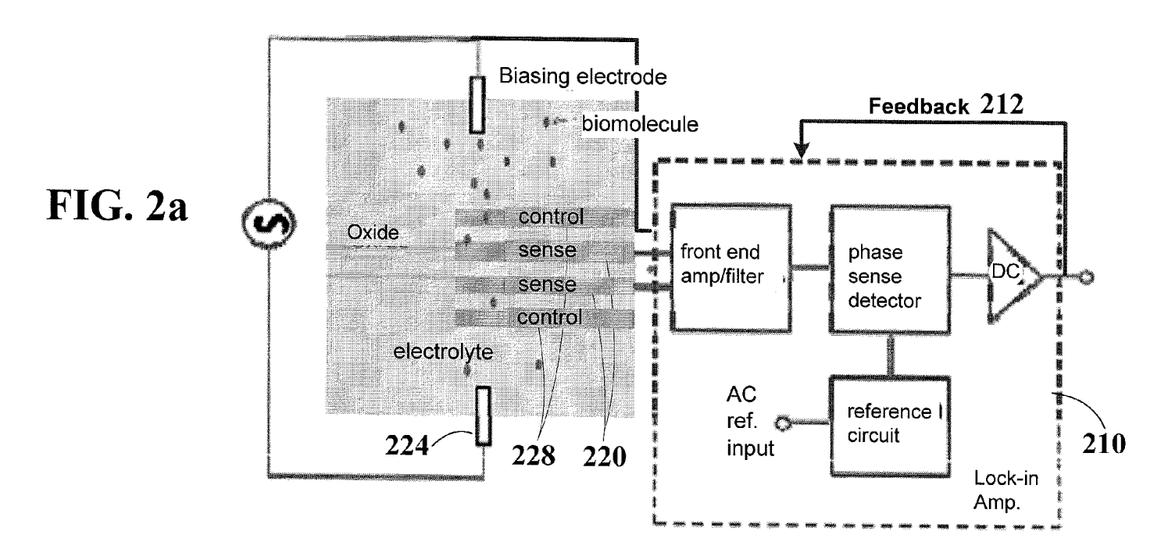
FIGS. 2a and 2b are illustrations of alternative biosensor sensor devices, according to the present disclosure.
Figure 2B:
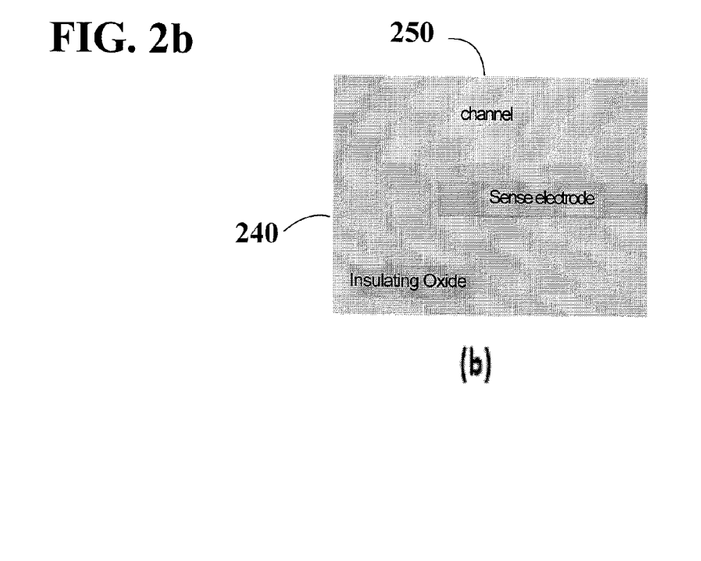

FIGS. 2A and 2B are illustrations of alternative biosensor sensor devices, according to the present disclosure. FIG. 2A is a simplified block diagram (from a top view) of a circuit-based biosensor sensor device having a peripheral lock-in amplification circuit 210 with a line 212 for the feedback signal used for the lock-in technique appropriate for the modulation applied at control electrodes 228, as would be appreciated by the skilled artisan. Rather than using a single charge-sense electrode, the biosensor sensor device of FIG. 2A uses a pair of electrodes 228 but otherwise similar voltage biasing via electrodes 220.

FIG. 2B provides a front view of the substrate (or slab) 240 of another biosensor sensor device, according to the present disclosure, in which the channel 250 traverses over the (dielectrically-insulated) sense electrodes. The skilled artisan would appreciate that aspects of embodiments disclosed herein need not be limited to convention semiconductive substrates; thus, while the slab 240 is illustrated as a substrate-like material having an insulating-oxide, the term "slab" is a more generic term that includes such specific substrates as well as other forms and materials (e.g., plastic) which can be used to support such structures as the channels, electrodes, etc.

In alternative or complementary embodiments (e.g., similarly described in Appendix B of the above-noted provisional document), the signals provided from the sense electrodes 228 can be passed to respectively assigned (optionally low-noise) amplifiers for processing the signal paths along dedicated channels via a signal process circuit. In one more specific embodiment, the signal process circuit receives the output signals via the amplifiers along such dedicated channels and processes the signals carried thereon by sampling and/or multiplexing these input signals.

Using this approach, sensor devices can be implemented in various forms. As just one example, such a sensor device employs a physical sensor channel stemming from a buried electrode to detect the charge of bio-molecules that are electrically driven through the surface channels.

For one such (experimental) sensor device, a surface channel (a width and height 100 nm and length ~1 micrometer) is fabricated using Micro-Electro-Mechanical Systems (MEMS) technologies and connected with two chambers that serve as reservoirs. An array of sense electrodes are buried at the bottom of the channels; they are then connected to read-out circuits that consist of charge sensitive amplifiers and following stages of signal multiplexing and processing units. Electrolyte solutions are introduced to fill in the channel and both reservoirs. Two biasing electrodes are placed in the solutions in each of the reservoirs. The analytes (charged biomolecules) are then introduced in one of the chambers. By applying voltages between the two biasing electrodes, the biomolecules travel across the channel to the other side by electrophoresis. When the biomolecules travel by the sense electrodes, image charges are induced in the electrode by field effect, which leads to signals in the read-out circuits. The multiplexing of signals from the multiple sense electrodes can be used to enhance the signal levels; and extract information based on travelling speeds of the analytes.

With the surface channel configuration using metal as sensing electrodes and the integrated read-out circuits being highly compatible with foundry IC and MEMS processes, this approach can lead to improved yield and reduced cost. Such long distance charge sensing is possible because the electrolyte screening is greatly suppressed in the presence of the ionic current flow. This scheme senses charge of each analyte molecule that travels across the sense electrode, i.e., its detection is at a single biomolecule level. This enables detection with very small sample volume, which can be advantageous compared to affinity type sensing schemes, whose signal is from an ensemble average of multiple analyte molecules attached to the sensor surface. Also multiple sense electrodes can be multiplexed to enhance signal levels using spatially correlated sampling techniques. Furthermore, based on the long range electrostatic interaction, the metal electrodes can be employed as actuators to control the movement of the bio-molecules. It has also been discovered herewith that the screening suppression effect is a function of the external electric field, which means the sensed signal can be electrically modulated. Based on this finding, AC modulation and lock-in techniques can be employed to dramatically enhance the sensitivities.

The operation principle of this type of charge sensor has been examined and discussed in Y. Liu, J. Sauer, and R. W. Dutton, "*Effect of electro-diffusion current flow on electrostatic screening in aqueous pores*," Journal of Applied Physics, vol. 103, p. 084701 (2008), where the charge sensing in a relatively large channel is feasible because of the electro-diffusion induced screening suppression effect. Underlying this effect is the Debye screening equilibrium being disrupted in the presence of ionic current flow. Using the same numerical technique, a feasibility study of a prototypical surface channel sensor is given in the following. Using a prototypical 3D device structure as in FIGS. 2a and/or 2b, an electrical bias V is applied between the cathode and anode to introduce the electro-diffusion flow. The bio-molecule is modeled as a water impermeable rod with its dimensions and charges corresponding to those of a 65-basepair dsDNA fragment. The ion transport is modeled by the coupled Poisson-Nernst-Planck equations. The sense electrode is modeled as a virtual ground. For various longitudinal locations of the bio-molecule, the percentage of the induced image charge at the sense electrode with respect to the total bio-molecular charge is computed. Along the vertical direction, the bio-molecule is placed 51 nm away from the sense electrode. The electrolyte concentration used in the simulations is 1 mM, corresponding to a Debye length of 10 nm.

Figure 5:
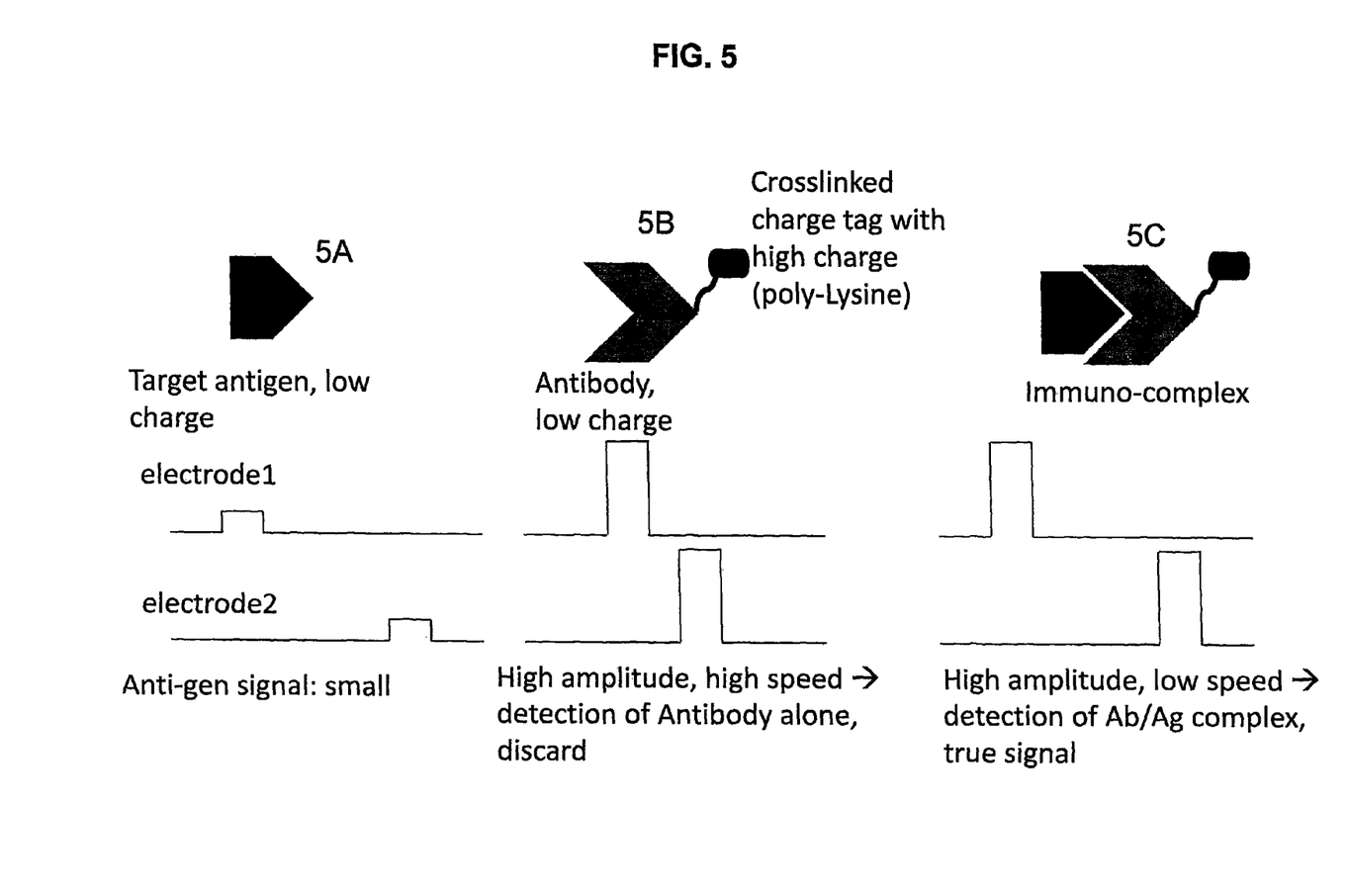
FIGS. 5a, 5b and 5c are diagrams useful in showing use of charge tags and antibody/antigen reaction to achieve high specificity.

Another possible variation is to use Si-nanowire (NW) or carbon nanotube (CNT) arrays as the sensing elements in replacement of the metal sensing electrodes (FIG. 5). In this scheme, the input charge signal is transduced and amplified to NW/CNT current signals right at the front end. Therefore, the parasitic effects are minimized: both signal levels and noise immunity can be greatly improved.

Yet another possible variation is to use affinity-type operation instead of the translocation-type. As in the common approach of affinity-based biosensors, the surface of the sensing elements (metal electrodes, Si-NWs or CNTs) can be chemically functionalized to immobilize analytes. In the common approach, there is only one reference electrode used in the electrolyte solution. The improvement to the approach is to intentionally introduce the ionic current flow to greatly enhance the signal levels; as studied in Y. Liu, K. Kilja, C. Heitzinger, and R. W. Dutton, "*Overcoming the screening-induced performance limits of nanowire biosensors: a simulation study on the effect of electro-diffusion flow,*" in IEDM Tech. Dig., San Francisco, pp. 491-494 (2008), the signal level can by enhanced by about an order of magnitude with ~100 kV/cm electric field in the solution. Furthermore, the AC modulation and lock-in techniques can be applied in this design as well.

Figure 3:
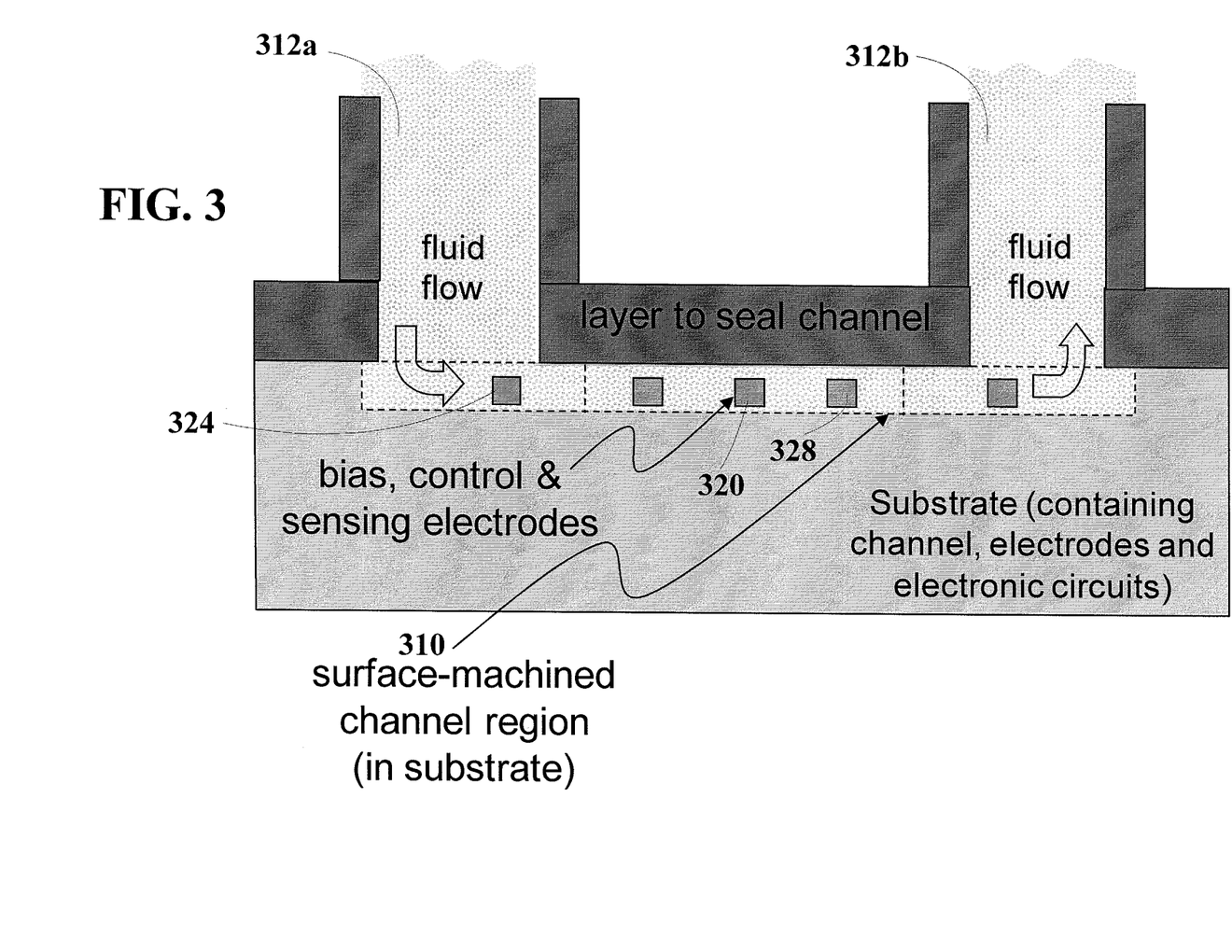
FIG. 3 is a cross-sectional view of an exemplary biosensor apparatus, according to the present disclosure.

FIG. 3 is a cross-sectional view of yet another exemplary biosensor apparatus, according to the present disclosure. As with the embodiments shown in FIGS. 1a-1c, bias electrodes 324 are located near or under the end of the channel 310, and modulation/control electrodes 328 are used when a lock-in amplification circuit (e.g., 210 of FIG. 2a) is used for enhancing detection capabilities. As illustrated in FIG. 3, the structures providing the reservoirs 312 and channel 310 at least in part implemented by different layers which can be built by various techniques which range from gluing plastic-molds to conventional semiconductor-processing techniques (layer deposition, etching, etc.). In this example, the lower portion of the channel 310 is indicated as being surface machined into the substrate which in some implementations includes a region in and/or on which integrated electronics (such as those shown in FIG. 2a) are incorporated for implementation of most or all of the device on a single integrated-circuit chip.

Figure 4:
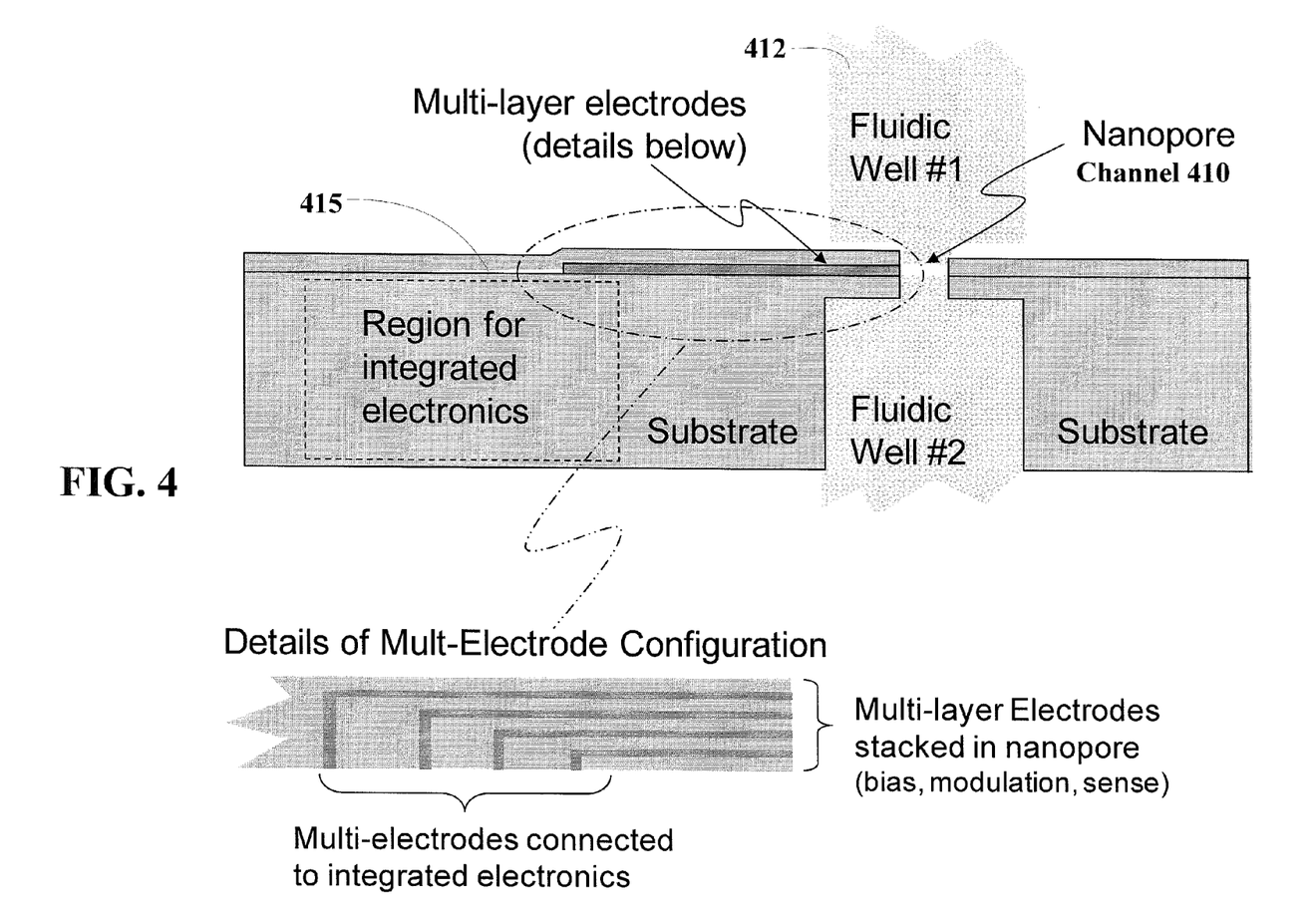
FIG. 4 is a cross-sectional view of an exemplary biosensor apparatus including a through-substrate (or slab) channel implementation, according to the present disclosure.

FIG. 4 illustrates yet another biosensor apparatus 400, according to the present disclosure, with illustration of a region in the substrate in which such integrated electronics are built. The biosensor apparatus includes a vertically-implemented (nanopore) channel 410 which guides the fluid via structures, above and below the substrate surface 415, for providing the reservoirs 412.

It will be appreciated that the width and length of the channel being illustrated in FIG. 4 and in the other figures vary depending on the implementation and/or the bimolecular application. For example, in particular embodiments, a nanopore channel is implemented with a width (thickness) in the range of about 5 nm-50 nm. Similarly, the channel length can vary widely and in one instance for the width being in the range 5 nm-50 nm, the channel length is about 300 nm. Flow for very small pores can be qualitatively different. For instance, for the larger pore sizes (10s to order or 100 Debeye length diameters), the electrode bias can dramatically change (and hence control) the fluid flow. As stated herewith in connection with exemplary experimental studies documented in the Appendices A, B, C and D included as part of the above-noted provisional patent document, these changes can be significant.

FIG. 5 is an illustration for embodiments, also consistent with the instant disclosure, showing use of charge tags and antibody/antigen reaction to achieve high specificity and high sensitivity. As illustrated in FIG. 5a, the target anti-gen molecule with low biological charge translocates through two sensing electrodes and induces a charge signal in each electrode. The time interval between the two correlated signals can be used to deduce its translocation velocity. The signal amplitude is low because of low charge.

In FIG. 5b, an antigen molecule specific to the target antibody is prepared so that it is cross-linked with a small tag molecule with high charge (poly-Lysine molecule in this example). This tagged antigen itself alone generates high signal amplitude as well as high translocation velocity because of the highly charged tag.

In FIG. 5c, when the tagged antigen specifically binds to the target antibody, the immunological complex has high charge and still generates high signal amplitude, but the larger size of the complex reduces its translocation velocity as compared to FIG. 5b. This unique, combined charge and velocity signature of the immunological complex is therefore useful to detect the presence of the target antibody, with its high specificity coming from the immunological reaction.

For embodiments consistent with the present disclosure, FIGS. 6a-6d are graphs (relating to the Appendix and its FIGS. 2(a)-2(d)) useful in showing that with proper electrical biasing, long-range electrostatics can be used to create zones that either accumulate or deplete charged species in solutions. For the accumulation case, this approach can be used to concentrate the biomolecule analytes and therefore enhance the sensitivity. For the depletion case, the approach can be used for different applications in desalination, e.g., to remove dissolved salts from sea water or brackish water. In other embodiments and applications, multiple electrodes and different application-specific structures can be used to develop application-specific sensitivities.

Figure 6A:
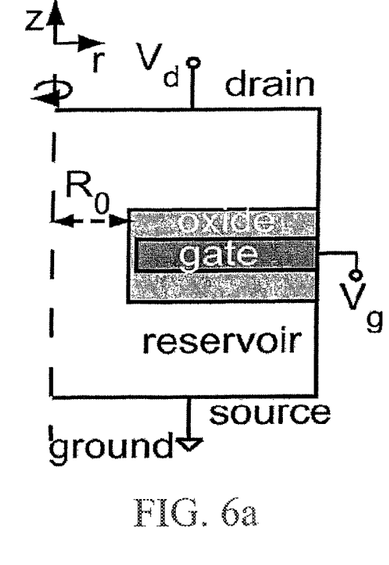
FIG. 6a is a block diagram and FIGS. 6b, 6c and 6d are graphs useful in showing the effect of proper electrical biasing in embodiments consistent with the present disclosure.

The limiting and overlimiting behaviors can be appreciated in connection with a specific Id-Vd curve having a constant $\Delta Vg$ of 1.5 V as in FIG. 6a. For comparison, two more curves are simulated by artificially increasing the solvent viscosity, while keeping the ion mobility unchanged. The nonlinearity is significantly reduced at higher viscosities, revealing the crucial role of the coupled fluid transport. In the following, four bias conditions are examined specifically for different Vd values, 0.1 V (A), 1.5 V (B), 3 V (C), and 4 V (D), for the case of nominal viscosity. The four conditions represent different conductance regimes: linear (A), limiting (B), and overlimiting (C and D).

Figure 6B:
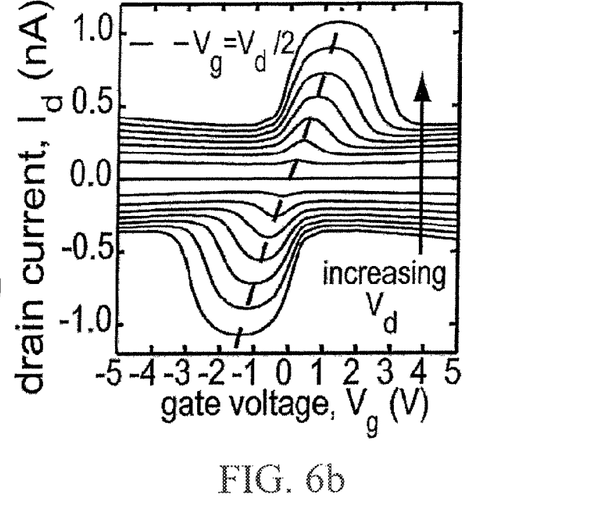

The limiting and overlimiting conductance is obtained by inspecting the normalized electrostatic potential, along the nanopore's longitudinal axis for the four bias conditions, as shown in FIG. 6b. The effect of gate potential ($\Delta Vg=1.5$ V) is to raise the potential inside the nanopore. This effect is the least significant in the case of low Vd (case A), which is expected because the transport is near equilibrium and the gate potential is strongly screened by counter-ions. The insignificant gate modulation is consistent with the linear Id-Vd characteristics in this regime. As Vd increases, the counter-ion screening become suppressed due to enhanced transport, leading to significantly increased gate modulation of channel electrostatics. As a result, in case B there is a highly asymmetric potential profile, where potential drop predominantly occurs at one side of the channel. In this regime, the current is limited by the strong gate modulation. As Vd increases further so that Vd/2≥ΔVg, the gate potential continues to be less screened but does not exceed its maximum limit ΔVg. Consequently, the relative impact of the gate modulation on the overall channel electrostatics becomes smaller, as shown by the reduced asymmetry in the normalized potential (cases C and D). In this regime, the symmetric biasing condition is reached in the limit as Vd approaches infinity. The ionic conductance therefore asymptotically approaches that under the symmetric biasing, thus exhibiting the overlimiting behavior.

Figure 6C:
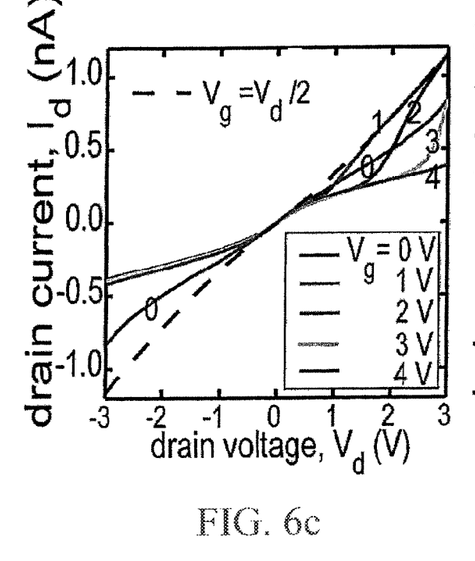

Concentration Polarization ("CP") is also observed as a result of the electrical gating. In FIG. 6c, the normalized total ion concentration, C=(C+C)/2C, is shown in algorithmic scale for the four bias conditions. In general, the ions deplete and accumulate at the bottom and top portions of the channel, respectively. The magnitude of CP is found to correlate strongly with the potential profiles in FIG. 2b. The CP is insignificant in case A and becomes stronger in case B. It then gradually reduces as the over limiting regime is reached in cases C and D. For such a correlation, the ion concentration is low in the high-field region and vice versa to maintain ionic flux continuity.

Figure 6D:
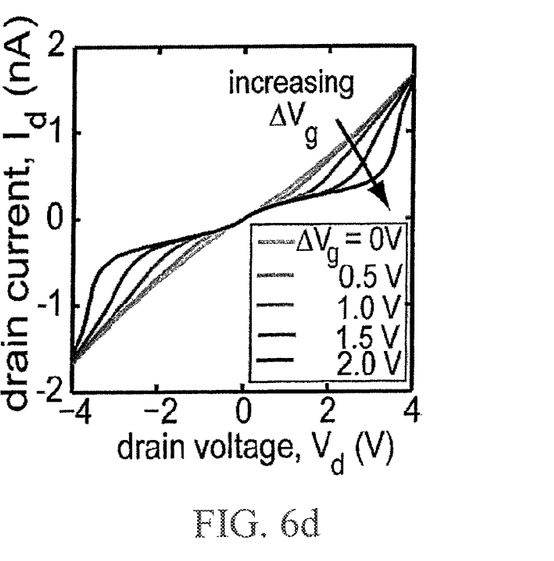

The fluid transport is examined in FIG. 6d, where the solvent velocity fields are shown for the four bias conditions. Induced electro-osmotic flow along the vertical direction is observed with an increasing magnitude from case A to case B. As the overlimiting regime is reached in case C, vortex formation is observed in the ion depletion zone at the bottom. The vortex flow is further enhanced in case D, and this trend continues as the symmetric biasing condition is asymptotically approached at higher level setting of $V_d$. The impact of coupled fluid transport via certain embodiments in the instant disclosure is to suppress the current in the limiting regime rather than to raise it in the overlimiting regime. As indicated via FIG. 6d, the conductance difference due to viscosity change is smaller in the overlimiting regime than in the limiting regime. It is believed that although their appearances are related, the vortex formation is not the dominant cause of the overlimiting conductance in such a gated nanopore device.

Experimental

Specific Examples and Embodiments

Certain aspects of the present disclosure involve introducing the flow of charged bio-molecules through synthetic pores and detecting induced potential signals at the pore walls. As a demonstration, having simulated a cylindrically symmetric model system where a piece of 60 base dsDNA is located at the center of an aqueous pore. The Poisson-Nernst-Planck (PNP) equations have been solved to model the ion transport across the pores. Such a continuum-based simulation approach has been carefully compared and validated with Brownian Dynamic simulation results for pores with radii $>\sim 2\Lambda_D$, which is the regime of interest here. A general partial differential equation solver, Prophet, has been used to solve those nonlinearly coupled model equations. A previous study was based on the same simulation platform to examine energetic preferred orientations of proteins (mitochondrial creatine kinase, type I hexokinase and cytochrome c) upon immobilization on charged surfaces. A. H. Talasaz, M. Nemat-Gorgani, Y. Liu, P. Stahl, R. W. Dutton, M. Ronaghi, and R. W. Davis, "Prediction of protein orientation upon immobilization on biological and nonbiological surfaces," Proc. Natl. Acad. Sci., 103(40) pp. 14773-8 (2006). Simulation results in this study involve the change of electrostatic potential due to the presence of the charged biomolecule is plotted. In equilibrium, Debye-Huckle charge-screening prevents the detection of potential changes beyond a few Debye lengths from the charged biomolecule. The Debye length at 1 mM KCl concentration is only 10 nm. When an electrical bias is applied to introduce electro-diffusion flow, the screening behavior is qualitatively different: the potential change becomes long-range and appreciable (~mV range) even inside the dielectric membrane. Such a dramatic suppression of the electrostatic screening is attributed to the current flow in the radial direction. It can be analytically derived that in the presence of current flow, a long-range, Ohmic-type behavior is superimposed to the Debye-Huckle type behavior in the solution of charge-induced potential drop. In order to examine the capability of the proposed device in spatially resolving charge profiles, a series of simulations were conducted for molecules, respectively with monopole and dipole (D~300 electron×nm) charge profiles, at different vertical locations in the center of the pore. The simulated profiles of potential change sensed in the membrane show signatures of the different charge profiles. It is also noted that the signal strength in the Dipole case can be 40× lower than that of the Monopole case, indicating high sensitivity will be needed for applications of spatially resolving charge profiles.

Further simulations have been carried out to study a realistic device structure that is under fabrication for this research project. In particular, the sensing metal electrode is sandwiched between two oxide insulator layers experimental embodiment and accounting for the circuitry operation of the charge sensing amplifier, the sensing electrode is connected to the virtual ground. Assuming the biomolecule charge is $-Q$, the induced charge in the metal electrode is $Q'=\beta Q$, which is essentially the amount of charge sensed by the amplifier circuitry. With the ratio factor $\beta$ calculated for different pore radii and biasing conditions, with moderate electrical biasing, the charge that can be sensed amounts to ~50% of the biomolecule charge for a 500 nm pore radius.

By using a foundry CMOS technology for the membrane substrate, the pore can be formed through a complex stack of metal and dielectric layers, which will be used to advantage in manipulating the charged biomolecule in the nanopore. In addition, the charge-sensing amplifier can be integrated on the same silicon substrate, adjacent to the pore, which minimizes the charge-signal loss due to parasitic capacitance. The CMOS technology includes a final deep dielectric-etch using the upper metal layer as a mask. Although this process could be used to etch the pore through the metallization stack, the minimum size of the pore would be 2 μm, which is too large for high-resolution charge detection. Therefore, a focused ion beam (FIB) can be used to etch the nanopore through the metallization stack; pore diameters of 250 nm or even smaller are feasible. A conventional deep-silicon dry etch or an anisotropic wet etch can be used to etch through the silicon substrate, in order to access the nanopore from the backside of the chip.

The low-noise, such as CMOS front-end charge amplifier has an area of 240×120 μm² and draws a bias current of 900 μA from the 1.8 V power supply, for a power consumption of 1.6 mW. Its design is largely based on front-end charge detectors used for nuclear imaging applications. G. De Geronimo, P. O'Connor, V. Radeka, and B. Yu, "*Front-end electronics for imaging detectors*," Nuclear Instruments and Methods in Physics Research A 471, pp. 192-199 (2001). The minimum detectable charge can be set by the amplifier's input-referred noise or by the noise current due to the ionic current through the nanopore. Since the amplifier is not constrained in its power dissipation for this application, within reasonable limits, the lowest equivalent noise charge (ENC) can be achieved by matching its input capacitance to be equal to the sense-electrode and parasitic capacitances. For an example nanopore, this capacitance is approximately 70 fF. Assuming a typical noise model for the amplifier, the input-referred noise voltage has a root-mean-square value of around 10 µV, over a measurement bandwidth of 1 kHz to 1 MHz, which translates into an ENC=9 electrons.

The presence of a DC ionic current through the nanopore is also a source of noise, which must be considered in estimating the minimum detectable charge. The impedance field method can be used to estimate the ionic current-induced charge noise at the sense electrode, using a technique similar to that used to model the gate-induced noise current in MOS transistors. F. Danneville, H. Happy, G. Dambrine, J.-M. Belquin, and A. Cappy, "*Microscopic noise modeling and macroscopic noise models: how good a connection?*," IEEE Trans. On Electron Devices, vol. 41, no. 5, pp. 779-786 (May 1994). Current fluctuations across the pore couple to the sense electrode and contribute to an equivalent input-referred charge noise, when integrated over the measurement bandwidth. The estimated ENC from this source is 25 electrons, which dominates the amplifier's input-referred noise. This result is very encouraging, since it indicates that single-stranded DNA can be detected with about 15 base pairs (30 electrons).

The multiple electrodes in the walls of the nanopore allow the electrostatic manipulation of the charged biomolecule's translocation through the pore. By using lock-in techniques (such as phase-locked/frequency-locked loop circuits), enhanced sensitivity can be achieved by limiting the measurement bandwidth.

According to another important aspect of the disclosure, integrated sensors are developed for direct detection of single target molecules by leveraging a nanotechnology-enabled type of sensing mechanism for quantifying the net charge of biomolecules passing through a nanoscale confined geometry. Here, a first characterization of the electrical property of the nanopore front-end and then the integrated platform. After the optimization of the sensor for an intended application, use of the device for detection of target DNAs hybridized to the specific probes. Finally, use of the multi-electrode actuation strategies for increasing the detection limit of the device with the final goal of counting the DNA bases with single base resolution.

A first more specific example involving the fabrication and characterization of charge sensitive nanopore devices: characterization of MEMS nanopore devices that are already fabricated without integrated electrical circuitry; and integration of the electrical circuitry with the nanopore device to increase the detection sensitivity.

The development of the herein described charge sensor embodiments involves coherent efforts in design, fabrication and characterization at both device and circuit levels to ensure that the front-end nanopores and the charge sensing circuits are properly designed and operational. Owing to the multi-layer electrode fabrication capabilities offered by the advanced IC technologies, a very large design space is expected to be explored to achieve optimal performance. Extensive characterization and testing on those already fabricated, prototypical MEMS devices as well as those integrated-circuitry devices under fabrication are necessary to provide important design parameters such as the noise floor and parasitic capacitances. In particular, the noise performance of the charge sensitive amplifier is dependent on front-end parasitic capacitance. Subsequent efforts to system performance optimization will be based on those design parameters.

Prototypical front-end nanopore devices (without integrated circuits) are fabricated using MEMS fabrication process. FIB techniques are used to create pores in those devices. SEM imaging is used to examine the size and shape of the pores, thus giving useful information on the range of pore sizes that are manufacturable with FIB. The electrical testing of such devices is then performed by connecting external AC/noise analyzers to the sensing electrode through wire bonding. Biosensor devices with integrated amplifier circuit are fabricated using advanced IC process. In particular, various design schemes can be implemented by utilizing the multi-layer electrode fabrication capabilities. An actual layout design of integrated sensors can use 0.18 µm CMOS technology with a low noise amplifier occupying an area of 240 um×120 um with a power consumption of 1.6 mW included and fabricated as part of the 0.18 µm CMOS process. As an example experiment, the primary limit on their proximity to the pores allows at least a 100 um electronics exclusion radius for the backside etch. The electrode designs range from a single electrode to a three-layer 6-electrode stack. Multiple electrode stacks allow enhanced time domain resolution as well as electrostatic control of the charged target molecule. After the fabrication process at the foundry facilities, these nanopore test chips have a backside cavity etch (200 µm diameter) to remove the substrate silicon around the pore sites. Then the nanopores are precision etched by FIB from the front-side, through the CMOS metal stack. After the FIB post-processing step, the nanopore sensor fabrication is complete, with optional testing to characterize parasitic capacitance, noise floor including the electronic noise component and sensitivity of the charge-sensing amplifier circuit.

For targeted minimum detectable signal of the integrated sensors at an arbitrarily-selected level of sub-100 electrons, a significant area of the fabricated sensor chip may need to be immersed in the ionic solution. For example, a poorly-selected/implemented O-ring seal used in a nanopore implementation may result in large parasitic capacitance and significant coupling of the ionic solution noise. Solutions include (i) using IC processes to increase the oxide layer thickness to reduce parasitic capacitance; and (ii) introduction of ionic solution using hypodermic needles which have much reduced contact area. Also, because the system minimum detectable signal is limited by the noise, particularly flicker noise, in the electronic amplifier circuit, buried channel MOSFETs are used as active elements in the amplified design. The buried channel MOSFETs are known to significantly reduce the flicker noise, as shown in previous extracellular action potential study. S. Ingebandt, "*Characterization of the cell-transistor coupling*," dissertation thesis, Johannes Gutenberg University Mainz, Germany (2001).

A second specific example involves the detection of the target DNA by charge nanopore devices. To develop an electrical sensor for label-free detection of single target DNA molecules, the proposed platform can be used for many genomic biomarker detection applications, such as viral and bacterial detection, without any PCR amplification step. This can be achieved by incubating the target DNAs with their specific probe oligonucleotides and employing nanopore charge sensing/sensor to detect the hybridization event by counting the net charge of each translocating DNA molecules. The nanopore charge sensor can detect the translocation events of the DNA molecules passing through the pore, with a train of pulses at the output of the integrated charge sensor. Then the charge sensor is used to distinguish ssDNA molecules from dsDNA. Initially, the electrical signals due to the translocation of a 1 kb PCR product are recorded and compared to the signals from the 1 kb ssDNA. Pulses were then realized with twice the amplitude for double-stranded PCR products. Subsequently, a gradual reduction of the length of DNA strands to measure the minimum detection limit of the device. Based on this information, a specific probe is designed so that the charge sensor can detect its hybridization to the target DNA.

When such a device is used for analyzing DNA molecules, there is a non-desirable interaction between translocating DNA and the electrode in the nanopore and possible electrochemical reactions. Alternative post-processing steps are implemented to passivate the sensing electrode that is exposed to the solution. Such surface treatments may involve deposition of metal oxide insulating layers by atomic layer deposition or surface chemistry treatment. The electrode passivation also minimizes Faradic current component across the interface. Also, if the detection limit of the device is not sufficient, the salt concentration is lowered in the solution to further reduce the charge screening effect and increase the induced charge.

In a third specific example, measuring of the DNA length by counting the DNA charges with the final goal of single base resolution and then evaluating the resolution of the charge sensor in quantification of the number of DNA bases. The sensitivity of the sensor is enhanced by multiple readout of the charge by multiple electrodes in the nanopore; electrical focusing of the DNA to the nanopore wall; and electrical-control of the DNA translocation speed by using multiple electrodes in the pore.

The ability to measure DNA charge to single electron precision results in quantification of DNA length to single base level, which enables important biological and medical applications. This challenging aspect is an important achievement of the sensor.

In one example approach, this aspect is implemented with aggressive signal detection and processing to dramatically improve SNR, e.g., by using any of various detection schemes. As examples: (a) Multiplexing: multiple metal layers used as independent sensing electrodes, each connected to its own amplifier and analog-to-digital converter (ADC). The multiple signals are multiplexed and processed in a digital signal processing (DSP) unit. The time delayed signals can be correlated to provide enhanced signal. (b) Deceleration: auxiliary electrodes are used to create a drift region in one segment of the aqueous pores, where the electrical field is small by design. For nanopores without such drifting designs, the DNA translocation time is usually in the sub-millisecond range. The purpose of this example design is to increase the dwelling time of DNAs in the drift region where the sensing electrode is, so that the actual signal sampling is enhanced. (c) Steering: with the suppressed screening effect, electrical field is introduced in the transverse planes so that, with the suppressed screening effect, the charged biomolecules can be electrically steered closer to the surface of the sensing electrode for improved signals.

As an alternative to enhance the above signal detection schemes and facilitate achieving resolution down to the signal electron level, AC-based signal detection is introduced to further boost sensitivity. Using this approach: (a) the charge sensing can be moved away from the low-frequency regime where flicker noise usually compromises signal detection; and (b) advanced lock-in amplification techniques can be employed, which have been broadly used in instrumentations to extract signals for SNR, for the experimental embodiments, as low as −60 dB.

By correlating signals from two or more sense electrodes, the bio-molecule velocity can be measured, i.e., besides the charge information, to also obtain the size information simultaneously. That means multiple parameters are available to identify the target. Experimental work has been focused on nanopore bio-sensors using the electro-diffusion effect. A new device fabrication process with protective Atomic Layer Deposition coatings on 500 nm size, photo-lithographically-defined pores can be used to improve the yield significantly, e.g., up to 80%. Using custom charge sense amplifier circuits or commercially-available circuits, significant biological sensing advancements can be realized. Also, for testing the operation principles, silicon nanowire prototypes are believed to be useful.

In accordance with yet further aspects, it has been discovered herewith that the movement of bio-molecules and ionic species can be controlled on this platform, i.e. nanochannels with side electrodes, based on the same or similar long-range electrostatic effect.

Based on other practical applications, the present disclosure is also directed to the following embodiments (including uses) based upon and leveraging from many of the previously discussed aspects, alone and/or in combination. First, use of a nanostructure as described above is not necessarily to be functionalized by a molecule type. In this case, the sensing mechanism is used to detect the charges of biomolecules flowing by the nanostructure rather than of those attached to the nanostructure. An example is the use of silicon nanowires or carbon nanotubes to replace the sensing metal electrodes (e.g., 320 in FIG. 3). As compared to the metal electrodes, the silicon nanowires or carbon nanotubes have their intrinsic trans-impedance gain at the very front end, which helps to minimize parasitic and offers better sensitivity.

As another aspect, by correlating signals from two or more sensing electrodes or nanostructures, the bio-molecule translocation velocity can be deduced in addition to its charge. The combined signature of velocity and charge provides high-quality identification of bio-molecules as compared to charge signal alone. One example of using this combined signature is described in FIG. 5. Use of the nanochannels with control electrode arrays, as illustrated in connection with the example of FIG. 2a, to electrically modulate the concentration of ions or charged molecules. The channel size is not limited by the Debye screening length as set forth herein.

Yet another aspect involves electrical biasing of the control electrode arrays to create solution zones between the electrodes with either depleted or accumulated concentrations of ions or charged molecules depending on the biasing schemes. The depletion and accumulation modes of operation can be used together and also used disparately in entirely different domains.

Other embodiments use electrical biasing in different manners. In one such embodiment, two control electrodes are used to create a solution zone between them, where the electrical field along the channel direction is high. In this zone, the ion concentration is depleted because of the high electrical field in order to maintain ionic flux continuity. The application of this depletion mode operation includes water desalination or de-ionization.

In another embodiment of this type, electrical biasing of two control electrodes is used to create a solution zone between them, where the electrical field along the channel direction is low. In this zone, the ion concentration is accumulated because of the low electrical field in order to maintain ionic flux continuity. Applications of this accumulation mode operation include biological sample pre-concentration.

In yet other embodiments, side channels are connected to the depletion or accumulation zones to extract out the solution of depleted or accumulated concentrations of ions or charged molecules. The extraction can be achieved using either pressure or voltage difference.

These above-described embodiments can be used alone or in various combinations.

Each of the Appendices (A, B, C and D) of the above-noted Provisional Patent document includes further experimental embodiments and features described and illustrated in connection with the above-described embodiments. These embodiments and features can be implemented as described or, as would be recognized, aspects thereof can be used in a variety of combinations. For further background information regarding charge detection of bio-molecular substances and/or affinity-type approaches to bio-molecule detection, reference may be made to the references listed in each of the attached Appendices A, B, C and D. For example, U.S. Pat. No. 6,413,792 (Ultra-Fast Nucleic Acid Sequencing Device and a Method for Making and Using the Same) and U.S. Pat. No. 7,001,792 (Ultra-Fast Nucleic Acid Sequencing Device and a Method for Making and Using the Same) provide ample discussion of previous structures and methods in specific DNA-directed applications. The article, *Effect of Electrodiffusion Current Flow on Electrostatic Screening in Aqueous Pores*, J. Appl. Phys. 103, pp. 084701-1-03 (2008), provides a mathematical discussion of the Debye-Huckel theory and charge sensing being limited to within a few Debye lengths from the biomolecules. Each of these references is fully incorporated herein by reference, generally and specifically.

Further, the Appendix attached hereto (forming part of the instant patent document) and entitled, Limiting and overlimiting conductance in field-effect gated nanopores, forms part of this patent document and also is incorporated by reference as further describing the above and related embodiments, uses and applications by way of its recent publication bearing the same title: Y. Liu, D. Huber, and R. Dutton, Appl. Phys. Lett. 96, 253108 (2010).

While the present invention has been described with reference to several particular example embodiments, those skilled in the art will recognize that many changes may be made thereto without departing from the spirit and scope thereof. The present invention is applicable to a variety of sensor implementations and other subject matter, in addition to those discussed above.

What is claimed is:

1. An apparatus comprising:
a substrate securing a channel located along a surface of the substrate, the channel having an effective width that is not limited by the Debye screening length;
at least one reservoir configured for containing and presenting a sample having bio-molecules for delivery in the channel;
a first electrode and a second electrode, each of the electrodes configured for electrically coupling a charge in the sample to enhance ionic current flow therein;
at least one sense electrode structure including one buried electrode to detect charges of the bio-molecules that are electrically driven along surfaces of the channel and located along the channel, and configured for sensing a characteristic of the biological sample at least partly based on electrostatic interaction between the enhanced ionic current flow of the sample and said at least one sense electrode structure,
wherein the at least one sense electrode structure, with the first and the second electrodes, is configured and arranged to facilitate detection of the bio-molecules based on variable voltage bias conditions; and
circuitry, including a charge-signal circuit coupled to said at least one sense electrode structure, for processing a signal carried therefrom and providing an output indicative of a type of the bio-molecules delivered in the channel.

2. An apparatus comprising:
a substrate securing a channel located along a surface of the substrate, the channel having an effective width that is not limited by the Debye screening length;
at least one reservoir configured for containing and presenting a sample having bio-molecules for delivery in the channel;
a first electrode and a second electrode, each of the electrodes configured for electrically coupling a charge in the sample to enhance ionic current flow therein;
at least one sense electrode structure including one buried electrode to detect charges of the bio-molecules that are electrically driven along surfaces of the channel and located along the channel, and configured for sensing a characteristic of the biological sample at least partly based on electrostatic interaction between the enhanced ionic current flow of the sample and said at least one sense electrode structure; and
circuitry, including a charge-signal circuit coupled to said at least one sense electrode structure, for processing a signal carried therefrom and providing an output indicative of a type of the bio-molecules delivered in the channel.

3. The apparatus of claim 2, wherein said at least one reservoir includes a first reservoir and a second reservoir, each of the first and second reservoirs fluidly-coupled to the channel.

4. The apparatus of claim 3, wherein the first electrode and the second electrode are respectively located in the first reservoir and in the second reservoir.

5. The apparatus of claim 2, wherein the channel has an effective width that is greater than or equal to about 200 nm.

6. The apparatus of claim 2, wherein the at least one sense electrode structure includes a pair of electrodes buried in the substrate, including said one buried electrode, adjacent the channel and arranged for charge sensing and bio-molecule movement control via a modulation technique.

7. The apparatus of claim 2, further including nanostructures disposed along the channel for sensing charges of the bio-molecules;
wherein the at least one sense electrode structure is configured using a plurality of additional sense electrodes, each driving an input of a sense amplifier; and
wherein the charge sensing is not limited by electrolyte screening.

8. The apparatus of claim 2, wherein the channel is a lateral channel including at least one of a micro-machined surface channel and a vertical channel.

9. The apparatus of claim 2, wherein the output is indicative of a charge detection of bio-molecular substances for medical diagnostic applications.

10. The apparatus of claim 2, wherein the channel is configured and arranged to transfer biomolecules across the channel to the other side of the channel by electrophoresis.

11. The apparatus of claim 2, further including a modulation circuit configured and arranged to provide a modulation signal via the first and the second electrodes, and wherein the charge-signal circuit includes a lock-in detection circuit configured and arranged to lock onto the modulation signal.

12. The apparatus of claim 2, wherein the at least one sense electrode structure is configured and arranged to provide AC modulation and a lock-in technique.

13. The apparatus of claim 2, wherein the at least one sense electrode structure is configured and arranged to change resistance in the presence of a certain type of complementary molecule.

14. The apparatus of claim 2, wherein the apparatus includes dedicated channels, and the at least one sense electrode structure is configured and arranged to pass signals to an amplifier for processing the signal paths along the dedicated channels.

15. The apparatus of claim 2, wherein an electrical bias voltage is applied between the first electrode and the second electrode to introduce an electro-diffusion flow.

16. The apparatus of claim 2, wherein the at least one sense electrode structure includes at least one of a Si-nanowire and a carbon nanotube array, the Si-nanowire or carbon nanotube array configured and arranged to transduce and amplify an input charge signal to Si-nanowire or carbon nanotube current signals.

17. The apparatus of claim 2, wherein the at least one sense electrode structure includes at least one sensing element, wherein a surface of the at least one sensing element is chemically functionalized to immobilize analytes.

18. The apparatus of claim 1, wherein the channel has a width between 5 nm-50 nm.

19. The apparatus of claim 2, wherein the at least one sense electrode structure includes two sensing electrodes, and wherein a target anti-gen molecule translocates through the two sensing electrodes to introduce a change signal in each sensing electrode.

20. The apparatus of claim 2, wherein the at least one sense electrode structure, with the first and the second electrodes, is configured and arranged to accumulate or deplete charged species in a solution.

21. The apparatus of claim 20, wherein ions deplete at a bottom portion of the channel and accumulate at a top portion of the channel.

22. The apparatus of claim 2, wherein the at least one sense electrode structure, with the first and the second electrodes, is configured and arranged to remove dissolved salts from a solution.

23. The apparatus of claim 2, wherein the at least one sense electrode structure, with the first and the second electrodes, is configured and arranged to facilitate detection based on variable voltage bias conditions and as a function of solvent viscosity and ion mobility.

24. The apparatus of claim 2, wherein the output indicative of a type of the bio-molecules delivered in the channel includes a combined signature, indicative of velocity and charge, that provides identification of the bio-molecule.

* * * * *